(12) United States Patent
Clark

(10) Patent No.: US 8,641,419 B2
(45) Date of Patent: *Feb. 4, 2014

(54) METHODS AND DEVICES FOR FIXED DENTAL RESTORATION

(76) Inventor: David J. Clark, Lakewood, WA (US)

(*) Notice: Subject to any disclaimer, the term of this patent is extended or adjusted under 35 U.S.C. 154(b) by 222 days.

This patent is subject to a terminal disclaimer.

(21) Appl. No.: 12/180,393

(22) Filed: Jul. 25, 2008

(65) Prior Publication Data

US 2009/0029324 A1  Jan. 29, 2009

Related U.S. Application Data

(60) Provisional application No. 60/951,804, filed on Jul. 25, 2007.

(51) Int. Cl.
*A61C 5/04* (2006.01)

(52) U.S. Cl.
USPC .............. 433/219; 433/39; 433/136; 433/215

(58) Field of Classification Search
USPC ........... 433/39, 136, 138, 148, 149, 218, 219, 433/215
See application file for complete search history.

(56) References Cited

U.S. PATENT DOCUMENTS

| | | | |
|---|---|---|---|
| 2,090,904 A * | 8/1937 | Singer | 433/148 |
| 2,629,930 A * | 2/1953 | Lane | 433/39 |
| 3,636,631 A * | 1/1972 | Tofflemire | 433/149 |
| 3,934,348 A | 1/1976 | Janjic | |
| 3,974,567 A | 8/1976 | Ridgeway | |
| 4,337,041 A | 6/1982 | Harsany | |
| 4,347,174 A | 8/1982 | Nagase et al. | |
| 4,443,197 A | 4/1984 | Fusayama et al. | |
| 4,465,462 A | 8/1984 | Ticknor | |
| 4,468,199 A | 8/1984 | Weikel | |
| 4,473,354 A | 9/1984 | Rigaud | |
| 4,504,230 A | 3/1985 | Patch | |
| 4,514,174 A | 4/1985 | Dougherty et al. | |
| 4,551,100 A | 11/1985 | Fischer | |
| 4,654,007 A | 3/1987 | Sigler et al. | |
| 4,685,969 A * | 8/1987 | Schmid et al. | 106/35 |
| 4,704,087 A * | 11/1987 | Dragan | 433/39 |
| 4,871,311 A | 10/1989 | Hagne | |
| 4,909,736 A | 3/1990 | Ritter | |
| 5,104,317 A | 4/1992 | Riazi | |
| 5,106,303 A | 4/1992 | Oden et al. | |
| 5,525,059 A | 6/1996 | Lee | |
| 5,707,236 A | 1/1998 | Swanson et al. | |

(Continued)

*Primary Examiner* — Robyn Doan
*Assistant Examiner* — Tatiana Nobrega
(74) *Attorney, Agent, or Firm* — Quarles & Brady, LLP

(57) ABSTRACT

This invention relates to methods and devices for restoring teeth using fixed restorations. In particular, the invention provides a system, kit, and devices for the management of interproximal areas for traditional cementation and/or bonding of dental crowns, onlays, inlays, veneers and bridges. In the method, a barrier is positioned in contact with the tooth being restored and an adjacent tooth to cover a section of the tooth being restored and to create separation of the tooth being restored and the adjacent tooth. Cement is applied to the first mating surface of the fixed restoration and/or to the second mating surface of the tooth, and the first mating surface of the fixed restoration and the second mating surface of the tooth are positioned adjacent each other to seat the fixed restoration on the tooth. The barrier covers a section of the tooth being restored to prevent cement from bonding to the section of the tooth. This eliminates the need to remove hardened cement from this section of the tooth.

9 Claims, 9 Drawing Sheets

(56) References Cited

U.S. PATENT DOCUMENTS

| | | | |
|---|---|---|---|
| 5,722,833 A | 3/1998 | Fischer et al. | |
| 5,944,884 A | 8/1999 | Panzera et al. | |
| 5,975,906 A | 11/1999 | Knutson | |
| 6,142,778 A * | 11/2000 | Summer | 433/39 |
| 6,206,697 B1 * | 3/2001 | Hugo | 433/155 |
| 6,234,793 B1 * | 5/2001 | Brattesani et al. | 433/39 |
| 6,402,514 B1 * | 6/2002 | Fischer et al. | 433/149 |
| 6,435,874 B1 * | 8/2002 | Hughes | 433/149 |
| 6,482,007 B2 | 11/2002 | Stanwich et al. | |
| 6,599,125 B1 | 7/2003 | Freilich et al. | |
| 6,619,956 B1 | 9/2003 | Weir | |
| 6,761,562 B2 | 7/2004 | Von Weissenfluh | |
| 6,890,176 B2 * | 5/2005 | Hahn | 433/39 |
| RE38,823 E | 10/2005 | Jensen et al. | |
| 7,033,173 B2 | 4/2006 | Coopersmith | |
| 7,083,412 B1 * | 8/2006 | Karapetyan | 433/148 |
| 7,121,828 B2 | 10/2006 | Fischer et al. | |
| 7,153,134 B2 | 12/2006 | Coopersmith | |
| 2004/0248064 A1 * | 12/2004 | Rodriguez del Val | 433/149 |
| 2005/0089813 A1 * | 4/2005 | Slone | 433/39 |
| 2005/0089814 A1 * | 4/2005 | Slone | 433/39 |
| 2005/0118554 A1 * | 6/2005 | Kilcher et al. | 433/141 |
| 2005/0255428 A1 * | 11/2005 | Coopersmith | 433/222.1 |
| 2005/0260543 A1 | 11/2005 | Dragan | |
| 2005/0271999 A1 | 12/2005 | Fishburne, Jr. | |
| 2006/0051722 A1 * | 3/2006 | Connell | 433/138 |
| 2006/0275734 A1 | 12/2006 | Vallittu et al. | |
| 2008/0064009 A1 * | 3/2008 | Clark | 433/148 |
| 2008/0064012 A1 * | 3/2008 | Clark | 433/226 |
| 2008/0241787 A1 * | 10/2008 | Hegedus | 433/149 |
| 2009/0104581 A1 * | 4/2009 | Simon | 433/149 |

\* cited by examiner

METHODS AND DEVICES FOR FIXED DENTAL RESTORATION

CROSS-REFERENCES TO RELATED APPLICATIONS

This application claims priority from U.S. Provisional Patent Application No. 60/951,804 filed Jul. 25, 2007.

STATEMENT REGARDING FEDERALLY SPONSORED RESEARCH

Not Applicable.

BACKGROUND OF THE INVENTION

1. Field of the Invention

This invention relates to methods and devices for restoring teeth using fixed restorations. In particular, the invention provides a system, kit, and devices for the management of interproximal areas for traditional cementation and/or bonding of dental crowns, onlays, inlays, veneers and bridges.

2. Description of the Related Art

In dentistry, fixed prosthodontics is a technique used to restore teeth using fixed restorations. Example fixed restorations include crowns, onlays, inlays, veneers, and bridges. Fixed restorations are normally fabricated away from the patient's mouth, and then cemented on a tooth being restored or on a dental implant. Crowns typically form the entire occlusal surface and the sides of the tooth being restored. Onlays typically cover all or part of the occlusal surface and sometimes portions of the sides. Inlays mainly cover central portions of the occlusal surface and may extend partially onto the sides. Veneers mainly cover only a side surface of a tooth. Bridges span a space where teeth are missing usually by connecting to fixed restorations on adjacent teeth.

After curing of the material that is used to cement a fixed restoration to a tooth, there often remains on side surfaces of the tooth an unwanted hardened mass of cured cement material that is difficult to dislodge. While dental instruments are available for removing the hardened cured cement from the side surfaces of the tooth, they are time consuming to use and may not be sufficiently effective. Hardened cured cement on the interproximal surface of the tooth being restored may be particularly difficult to remove due to the small interproximal space between adjacent teeth.

Furthermore, the interdental area is a historically problematic zone because of problems in evaluating and adjusting the contacts, controlling the physical presence of the gingiva (papilla/col) and controlling fluid contamination, along with the aforementioned significant problems of traditional cements or the newer composite cements that flow past the margins on to areas of the tooth being restored and the neighboring teeth.

Much effort can be expended to remove cement before it sets which can disturb the gingiva causing bleeding and cement contamination, or the cement can be mechanically harmed while it is setting, causing it to pull out from the margin or be compromised. Additionally the prosthesis (crown, bridge, veneer, onlay, or inlay) can move creating incomplete or incorrect seating resulting in poor fit, cement voids and air bubbles, bite problems, etc. As noted above, excess residual cured cement can be extremely challenging and time consuming to remove which may cause damaging to tooth, gingiva and prosthesis. There have been reports of residual cement that is inadvertently left in place causing post operative pain, swelling, chronic tissue inflammation resulting in poor esthetics, difficulty in flossing and periodontal inflammation with resulting reversible and irreversible periodontal break down.

Thus, there is a need for improved methods and devices for restoring teeth using fixed restorations wherein reduced amounts of cement are allowed to extend beyond the tooth-to-restoration margin when the fixed restoration is cemented to the tooth being restored.

SUMMARY OF THE INVENTION

The foregoing needs are met by the invention. In one aspect, the invention provides a method for restoring a natural or artificial tooth. By "artificial tooth", I also mean a dental implant. In the method, a portion of the tooth may be removed. A fixed restoration having a first mating surface substantially conforming to a second mating surface of the tooth is provided. A barrier/barricade is positioned in contact with the tooth being restored and an adjacent tooth to cover a section of the tooth being restored and to create separation of the tooth being restored and the adjacent tooth. Cement is applied to the first mating surface of the fixed restoration and/or to the second mating surface of the tooth, and the first mating surface of the fixed restoration and the second mating surface of the tooth are positioned adjacent each other to seat the fixed restoration on the tooth. The cement is then cured. In the method, the barrier/barricade covers a section of the tooth being restored to prevent cement from bonding to the section of the tooth. This eliminates the need to remove hardened cement from this section of the tooth.

In another aspect, the invention provides a method for restoring an artificial tooth root replacement, that is, a dental implant. In this method, the fixed restoration is implant supported. The fixed restoration has a first mating surface substantially conforming to a second mating surface of the implant. A barrier/barricade is positioned in contact with the implant to cover a section of the implant. Cement is applied to the first mating surface of the fixed restoration and/or to the second mating surface of the implant, and the first mating surface of the fixed restoration and the second mating surface of the implant are positioned adjacent each other to seat the fixed restoration on the implant. The cement is then cured. In the method, the barrier/barricade covers a section of the implant to prevent cement from bonding to the section of the implant. This eliminates the need to remove hardened cement from this section of the implant.

The fixed restoration may be formed from a material selected from porcelain, metallic materials (e.g., gold), porcelain fused to a metallic material, composite materials (e.g., particle filled polymeric materials), polymeric materials (e.g., acrylic materials), and ceramic materials. The fixed restoration may be a traditional lab created fixed restoration or may be produced on a chairside CAD/CAM designing and milling system such as that sold under the tradename CEREC by Sirona Dental Systems.

In one form, the body of the barrier has a first end portion, a second opposite end portion, and a middle portion connecting the first end portion and the second end portion. The body includes a first side surface having a first outwardly extending protrusion on the first end portion. The first side surface also has a second outwardly extending protrusion on the second end portion. The first protrusion and the second protrusion contact the tooth being restored when the barrier is positioned in contact with the tooth being restored. The first outwardly extending protrusion of the barrier can be spaced inward from a first end surface of the body of the barrier, and the second outwardly extending protrusion of the barrier can be spaced inward from a second end surface of the body of the barrier.

In another form, the body of the barrier has a first end portion, a second opposite end portion, and a middle portion connecting the first end portion and the second end portion. The middle portion includes a first spherical section, a second spherical section, and a central section connecting the first spherical section and the second spherical section in spaced relationship. The first spherical section and the second spherical section contact the tooth being restored when the barrier is positioned in contact with the tooth being restored. The first end portion can include a first section connecting the first spherical section of the middle portion and a second section of the first end portion. The second section of the first end portion extends laterally outward from the first section of the first end portion, and in one example form, the second section of the first end portion is disc-shaped. The second end portion includes a first section connecting the second spherical section of the middle portion and a second section of the second end portion. The second section of the second end portion extends laterally outward from the first section of the second end portion, and in one example form, the second section of the second end portion is disc-shaped. The central section of the barrier body can include concave lower side surfaces that fit snugly against lower regions of the interproximal surfaces of the tooth being restored and an adjacent tooth. The central section can include a concave bottom surface that fits snugly on the gingiva and compresses and displaces gingiva when the barrier is positioned between the tooth being restored and an adjacent tooth.

In one example form, the body of the barrier is dimensioned such that a bottom surface of the body contacts gingiva and a top surface of the barrier is positioned within 5 millimeters (most preferably within 0.75 millimeters) of a margin selected from a tooth-to-restoration margin, an implant-to-restoration margin, and an implant abutment-to-restoration margin when the barrier is positioned in contact with the tooth. The body of the barrier is dimensioned to create separation of the tooth being restored and an adjacent tooth.

The barrier can have a textured surface that allows the barrier to be moved toward or away from a margin selected from a tooth-to-restoration margin, an implant-to-restoration margin, and an implant abutment-to-restoration margin. The barrier can have an elastomeric surface that allows the barrier to be moved toward or away from a margin selected from a tooth-to-restoration margin, an implant-to-restoration margin, and an implant abutment-to-restoration margin.

In yet another aspect, the invention provides a method for restoring a natural or artificial tooth. The method includes providing a fixed restoration (such as a crown, onlay, inlay, veneer, or bridge) having a first mating surface substantially conforming to a second mating surface of the tooth; applying a flowable curable barrier material to a surface section of the tooth being restored and gingiva adjacent the tooth; curing the barrier material on the surface section and gingiva adjacent the tooth; applying a cement to the first mating surface of the fixed restoration and/or to the second mating surface of the tooth; and positioning the first mating surface and the second mating surface adjacent each other. In the method, a tooth-to-restoration margin is located adjacent the surface section. Preferably, the barrier material is positioned within 5 millimeters of the margin. Most preferably, the barrier material is positioned within 0.75 millimeters of the margin. The barrier material can include (i) a monomer or prepolymer and (ii) a curing agent. The barrier material can include a solvent such that the barrier material cures during evaporation of the solvent. The barrier material can be light curable.

Thus, it is an advantage of the present invention to provide a device that only allows minimal amounts of cement to extend beyond a margin (such as a tooth-to-restoration margin, an implant-to-restoration margin, and an implant abutment-to-restoration margin) when a fixed restoration is cemented to a tooth or an implant.

It is another advantage of the present invention to provide a device that covers enamel, dentin, cementum, an implant surface or an implant abutment surface adjacent a margin such that the enamel, dentin, cementum, implant surface or implant abutment surface is not covered with cement when the fixed restoration is cemented to the tooth being restored or the implant.

It is yet another advantage of the present invention to provide a device for restoring teeth using fixed restorations that lightly separates approximating teeth.

It is still another advantage of the present invention to provide a device for restoring teeth using fixed restorations that provides a barrier against fluid (e.g., blood, saliva) contamination.

It is yet another advantage of the present invention to provide a device for restoring teeth using fixed restorations that protects gingiva from laceration.

It is still another advantage of the present invention to provide a device for restoring teeth using fixed restorations that protects the gingiva from abrasion that may cause gingival bleeding.

It is yet another advantage of the present invention to provide a device for restoring teeth using fixed restorations that compresses and displaces gingiva.

It is still another advantage of the present invention to provide a device for restoring teeth using fixed restorations that provides a barricade to stop undesired flow of cement past margins on a tooth being restored or neighboring teeth.

It is yet another advantage of the present invention to provide a device for restoring teeth or an implant using a fixed restoration wherein the device is allowed to be placed slightly past the finish lines at approximately 0.75 millimeters to allow and create a feather edge bonding zone especially in the case of ceramo-enamel bonding or resin/enamel bonding.

It is still another advantage of the present invention to provide a device for restoring teeth using fixed restorations wherein the device has a textured surface that allows the device to be moved up or down a root or implant, toward or away from a tooth-to-restoration margin or an implant-to-restoration margin.

It is yet another advantage of the present invention to provide a device for restoring teeth or an implant using a fixed restoration wherein the device has an elastomeric surface that allows the device to be moved up or down a root or implant, toward or away from a tooth-to-restoration margin or an implant-to-restoration margin.

These and other features, aspects, and advantages of the present invention will become better understood upon consideration of the following detailed description, drawings and appended claims.

BRIEF DESCRIPTION OF THE DRAWINGS

Like reference numerals will be used to refer to like parts from Figure to Figure in the following description of the drawings.

DETAILED DESCRIPTION OF THE INVENTION

Turning to FIGS. 1-5T, there is shown various steps and devices in an example method according to the invention for restoring teeth using a fixed restoration such as a crown, onlay, inlay, veneer, or bridge. In a first step, the dentist locates a tooth 12 needing restoration. The dentist removes the decayed portion of the tooth 12 and leaves a mating surface 22 exposed. A material may be applied to the exposed mating surface 22 with the material bonding to the surface and serving as a fusible substrate for attachment of a fixed restoration thereto. Thereafter, the dentist makes a negative impression of the mating surface 22. The negative impression is used as a model to produce a positive impression of the previously prepared tooth needing restoration. Using this positive, the lab or the dentist fabricates a fixed restoration 24 having a mating surface 26 substantially conforming to the mating surface 22 of the tooth 12 requiring restoration (see FIG. 2). This fabrication of the fixed restoration 24 can involve any number of techniques known in the art. For example, porcelain material can be used to make the restoration 24. Metals (e.g., gold) and/or polymeric materials and/or ceramic materials can also be used to form the restoration 24. After the restoration 24 is formed, it is ready for installation on the patient's tooth 12.

Figure 1:
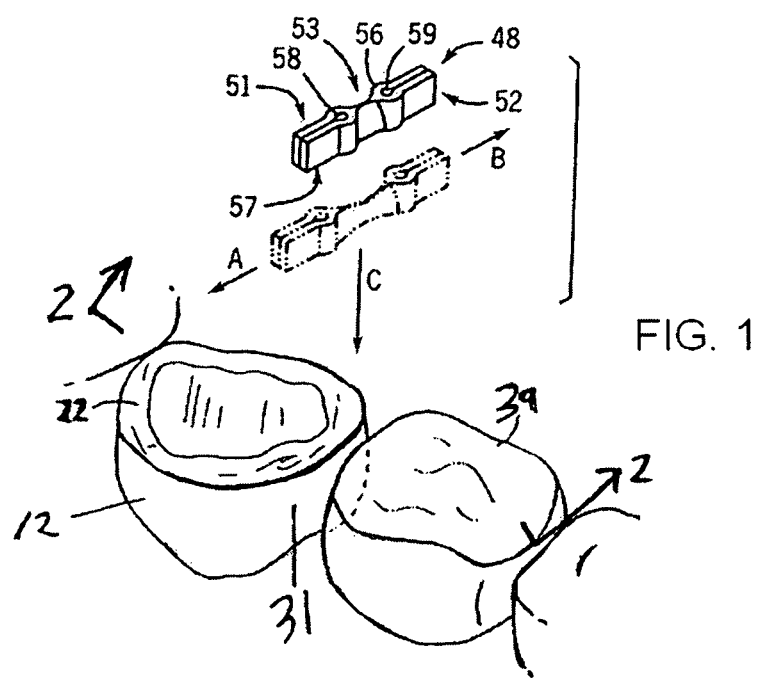
FIG. 1 top perspective view of the barrier/barricade insertion step of the method according to the invention.
Figure 2:
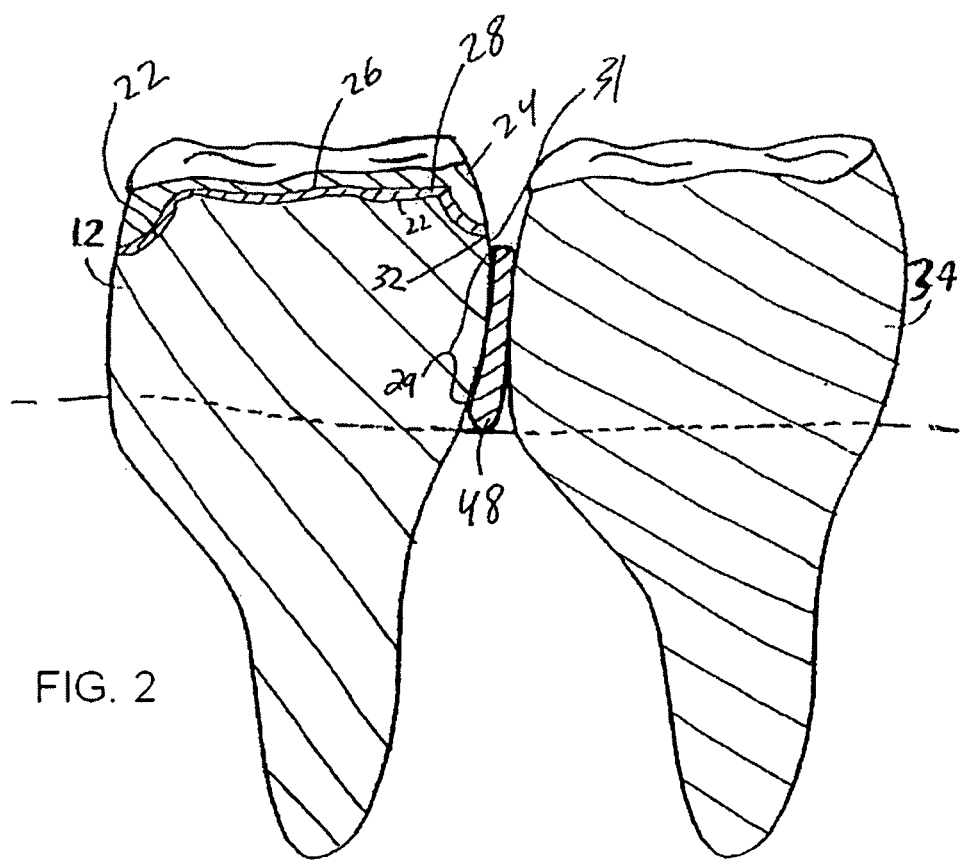
FIG. 2 is a cross-sectional view taken along line 2-2 of FIG. 1.
Figure 3:
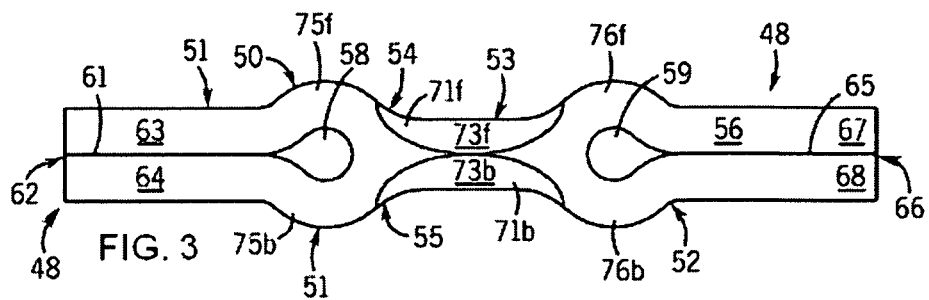
FIG. 3 is a top view of one embodiment of a barrier/barricade according to the invention.

Referring to FIGS. 1 and 2, a first step in the installation of the formed fixed restoration 24 is depicted. In this step, a barrier/barricade 48 is positioned in contact with the tooth 12 being restored and an adjacent tooth 34 to cover gingiva and a section 29 of the interproximal surface 31 of the tooth 12 being restored and to create separation of the tooth 12 being restored and the adjacent tooth 34. One example embodiment of a barrier/barricade 48 that can be used in the method of the invention will be now be described in further detail. Looking at FIGS. 1 and 3, the barrier/barricade 48 includes an elongated translucent (preferably transparent) elastic body 50 having a first end portion 51, a second opposite end portion 52, a middle portion 53 connecting the first end portion 51 and the second end portion 52, a first side surface 54, a second side surface 55, a top surface 56 and a bottom surface 57. The first end portion 51 has a first throughhole 58 extending from the top surface 56 to the bottom surface 57 of the barrier/barricade 48. The second end portion 52 has a second throughhole 59 extending from the top surface 56 to the bottom surface 57 of the barrier/barricade 48. The throughholes 58, 59 are an optional feature of the barrier/barricade 48. Therefore, the throughholes 58, 59 may be left out of the barrier/barricade 48.

The first end portion 51 includes an area 61 of material weakness that extends toward the top surface 56 and extends toward the bottom surface 57 and extends toward a first end surface 62 of the body 50. The area 61 of material weakness extends from the first throughhole 58 to the first end surface 62 of the body 50. This allows the first end portion 51 to be separated into separate end members 63, 64 by application of a separation force at the area 61 of material weakness of the barrier/barricade 48. Preferably, end members 63, 64 have a rectangular vertical cross-section. The area 61 of material weakness can be formed with a material of lower shear strength than the other material of the barrier/barricade 48, or can be formed by including perforations or other like open areas in the area 61 of material weakness. The area 61 of material weakness is an optional feature of the barrier/barricade 48.

The second end portion 52 includes an area 65 of material weakness that extends toward the top surface 56 and extends toward the bottom surface 57 and extends toward a second end surface 66 of the body 50. The area 65 of material weakness extends from the second throughhole 59 to the second end surface 66 of the body 50. This allows the second end portion 52 to be separated into separate end members 67,68 by application of a separation force at the area 65 of material weakness of the barrier/barricade 48. Preferably, end members 67, 68 have a rectangular vertical cross-section. The area 65 of material weakness can be formed with a material of lower shear strength than the other material of the barrier/barricade 48, or can be formed by including perforations or other like open areas in the area 65 of material weakness. The area 65 of material weakness is an optional feature of the barrier/barricade 48.

The top surface 56 of the body 50 of the barrier/barricade 48 includes a first pair of upper side-by-side depressions 71*f*, 71*b* in the middle portion 53 of the body 50, and the bottom surface 57 of the body 50 includes a second pair of analogous lower side-by-side depressions (not shown) in the middle portion of the body 50. The first pair of upper side-by-side depressions 71*f*, 71*b* include inwardly curved inner surfaces 73*f*, 73*b*, and the second pair of lower side-by-side depressions (not shown) include analogous inwardly curved inner surfaces (not shown).

In the barrier/barricade 48, the first side surface 54 of the body 50 includes a curved protrusion 75*f* located near the first throughhole 58 and a curved protrusion 76*f* located near the second throughhole 59. Likewise, the second side surface 55 of the body 50 includes a curved protrusion 75*b* located near the first throughhole 58 and a curved protrusion 76*b* located near the second throughhole 59. The barrier/barricade 48 can be formed from a translucent (preferably transparent) elastomeric material such as a silicone elastomer or a polyurethane elastomer.

The surface of the barrier/barricade 48 can comprise an elastomeric material such as a silicone elastomer or a polyurethane elastomer that allows the barrier/barricade 48 to be moved up or down a root or implant, toward or away from a tooth-to-restoration margin or implant-to-restoration margin during a restoration procedure. The surface of the barrier/barricade 48 can have a textured surface that allows the barrier/barricade 48 to be moved up or down a root or implant, toward or away from a tooth-to-restoration margin or implant-to-restoration margin during a restoration procedure. This allows the dentist to move the barrier/barricade 48 to adjust the distance of the top surface 56 of the body 50 of the barrier/barricade 48 from the tooth-to-restoration margin or implant-to-restoration margin. In one non-limiting example form, the textured surface may comprise continuous or discontinuous depressions on the surface of the barrier/barricade 48. Plastics molding techniques may be used to create the depressions.

Referring to FIGS. 1 and 2, the placement of the barrier/barricade 48 is shown during a method according to the invention for the restoration of a tooth 12. The dentist stretches the barrier/barricade 48 in directions A and B shown in FIG. 1. The barrier/barricade 48 can be stretched by inserting the ends of a pliers in the first throughhole 58 and the second throughhole 59 of the barrier/barricade 48 and opening the ends of the pliers. Alternatively, the dentist can grab and pull apart the end portions 51 and 52 of the barrier/barricade 48 in directions A and B shown in FIG. 1. The stretching of the barrier/barricade 48 leads to a thinning of the middle portion 53 of the barrier/barricade 48 such that the barrier/barricade 48 can be inserted between teeth 12 and 34 by movement in direction C of FIG. 1. The barrier/barricade 48 then biases the tooth 12 and the tooth 34 apart. The barrier/barricade 48 also covers the gingiva and the section 29 of the interproximal surface 31 of the tooth 12.

Figure 4:
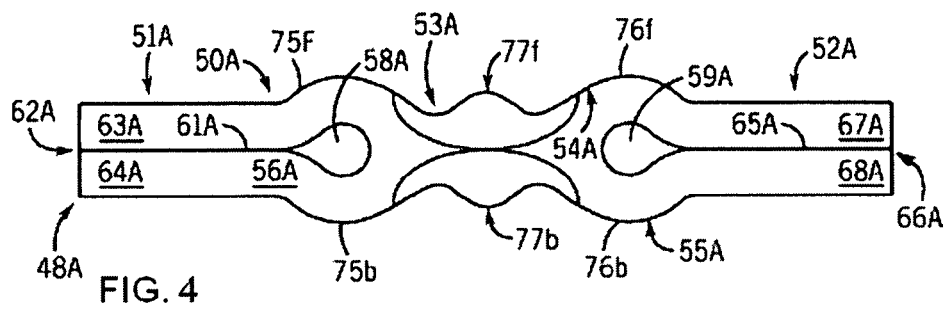
FIG. 4 is a top view of another embodiment of a barrier/barricade according to the invention.

Turning to FIG. 4, there is shown another embodiment of a barrier/barricade 48A which includes an elongated translucent (preferably transparent) elastic body 50A having a first end portion 51A, a second opposite end portion 52A, a middle portion 53A connecting the first end portion 51A and the second end portion 52A, a first side surface 54A, a second side surface 55A, a top surface 56A and a bottom surface (not shown). The first end portion 51A has a first throughhole 58A extending from the top surface 56A to the bottom surface of the barrier/barricade 48A. The second end portion 52A has a second throughhole 59A extending from the top surface 56A to the bottom surface of the barrier/barricade 48A. The throughholes 58A, 59A are an optional feature of the barrier/barricade 48A.

The first end portion 51A includes an area 61A of material weakness that extends toward the top surface 56A and extends toward the bottom surface and extends toward a first end surface 62A of the body 50A. The area 61A of material weakness extends from the first throughhole 58A to the first end surface 62A of the body 50A. This allows the first end portion 51A to be separated into separate end members 63A, 64A by application of a separation force at the area 61A of material weakness of the barrier/barricade 48A. Preferably, end members 63A, 64A have a rectangular vertical cross-section. The area 61A of material weakness is an optional feature of the barrier/barricade 48A.

The second end portion 52A includes an area 65A of material weakness that extends toward the top surface 56A and extends toward the bottom surface and extends toward a second end surface 66A of the body 50A. The area 65A of material weakness extends from the second throughhole 59A to the second end surface 66A of the body 50A. This allows the second end portion 52A to be separated into separate end members 67A, 68A by application of a separation force at the area 65A of material weakness of the barrier/barricade 48A. Preferably, end members 67A, 68A have a rectangular vertical cross-section. The area 65A of material weakness is an optional feature of the barrier/barricade 48A.

In the barrier/barricade 48A, the first side surface 54A of the body 50A includes a curved protrusion 75*f* located near the first throughhole 58A and a curved protrusion 76*f* located near the second throughhole 59A. Likewise, the second side surface 55A of the body 50A includes a curved protrusion 75*b* located near the first throughhole 58A and a curved protrusion 76*b* located near the second throughhole 59A.

In barrier/barricade 48A, the first side surface 54A of the body 50A includes a first curved protrusion 77*f* located near an intermediate vertical plane of the body 50A. Likewise, the second side surface 55A of the body 50A includes a second curved protrusion 77*b* located near the intermediate vertical plane of the body 50A. The curved protrusions 77*f*, 77*b* are beneficial as they provide contact with tooth surface that may have inward decay due to the age of the patient. The barrier/barricade 48A can be formed from a translucent (preferably transparent) elastomeric material such as a silicone or polyurethane elastomer.

The surface of the barrier/barricade 48A can comprise an elastomeric material that allows the barrier/barricade 48A to be moved up or down a root or implant, toward or away from a tooth-to-restoration margin or implant-to-restoration margin during a restoration procedure. The surface of the barrier/barricade 48A can have a textured surface that allows the barrier/barricade 48A to be moved up or down a root or implant, toward or away from a tooth-to-restoration margin or implant-to-restoration margin during a restoration procedure. This allows the dentist to move the barrier/barricade 48A to adjust the distance of the top surface 56A of the body 50A of the barrier/barricade 48A from the tooth-to-restoration margin or implant-to-restoration margin.

Figure 5:
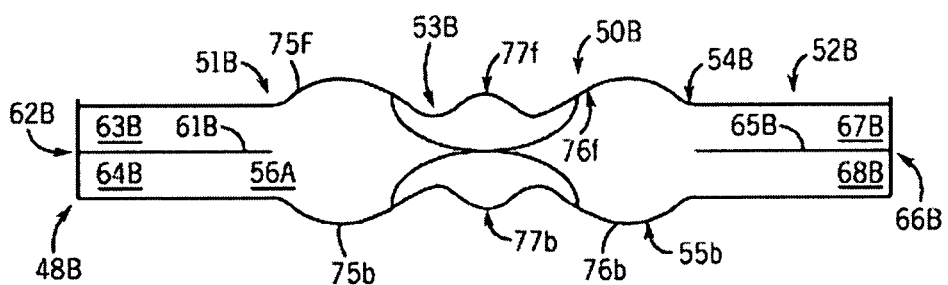
FIG. 5 is a top view of yet another embodiment of a barrier/barricade according to the invention.

Turning to FIG. 5, there is shown another embodiment of a barrier/barricade 48B which includes an elongated translucent (preferably transparent) elastic body 50B having a first end portion 51B, a second opposite end portion 52B, a middle portion 53B connecting the first end portion 51B and the second end portion 52B, a first side surface 54B, a second side surface 55B, a top surface 56B and a bottom surface (not shown).

The first end portion 51B includes an area 61B of material weakness that extends toward the top surface 56B and extends toward the bottom surface and extends toward a first end surface 62B of the body 50B. The area 61B of material weakness extends from an inner portion of the first end portion 51B to the first end surface 62B of the body 50B. This allows the first end portion 51B to be separated into separate end members 63B, 64B by application of a separation force at the area 61B of material weakness of the barrier/barricade 48B. Preferably, end members 63B, 64B have a rectangular vertical cross-section. The area 61B of material weakness is an optional feature of the barrier/barricade 48B.

The second end portion 52B includes an area 65B of material weakness that extends toward the top surface 56B and extends toward the bottom surface and extends toward a second end surface 66B of the body 50B. The area 65B of material weakness extends from an inner portion of the second end portion 52B to the second end surface 66B of the body 50B. This allows the second end portion 52B to be separated into separate end members 67B, 68B by application of a separation force at the area 65B of material weakness of the barrier/barricade 48B. Preferably, end members 67B, 68B have a rectangular vertical cross-section. The area 65B of material weakness is an optional feature of the barrier/barricade 48B.

In the barrier/barricade 48B, the first side surface 54B of the body 50B includes a curved protrusion 75f and a curved protrusion 76f. Likewise, the second side surface 55B of the body 50B includes a curved protrusion 75b and a curved protrusion 76b.

In barrier/barricade 48B, the first side surface 54B of the body 50B includes a first curved protrusion 77f located near an intermediate vertical plane of the body 50B. Likewise, the second side surface 55B of the body 50B includes a second curved protrusion 77b located near the intermediate vertical plane of the body 50B. The curved protrusions 77f, 77b are beneficial as they provide contact with tooth surface that may have inward decay due to the age of the patient. The barrier/barricade 48B can be formed from a translucent (preferably transparent) elastomeric material such as a silicone or polyurethane elastomer.

The surface of the barrier/barricade 48B can comprise an elastomeric material that allows the barrier/barricade 48B to be moved up or down a root or implant, toward or away from a tooth-to-restoration margin or implant-to-restoration margin during a restoration procedure. The surface of the barrier/barricade 48B can have a textured surface that allows the barrier/barricade 48B to be moved up or down a root or implant, toward or away from a tooth-to-restoration margin or implant-to-restoration margin during a restoration procedure. This allows the dentist to move the barrier/barricade 48B to adjust the distance of the top surface 56B of the body 50B of the barrier/barricade 48B from the tooth-to-restoration margin or implant-to-restoration margin.

Figure 5B:
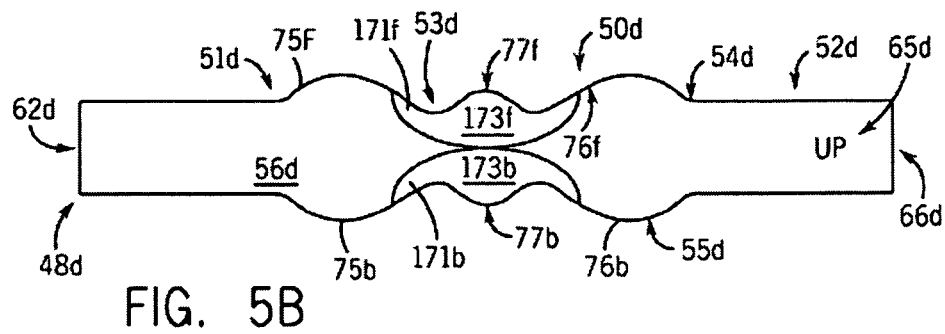
FIG. 5B is a top view of still another embodiment of a barrier/barricade according to the invention.
Figure 5C:
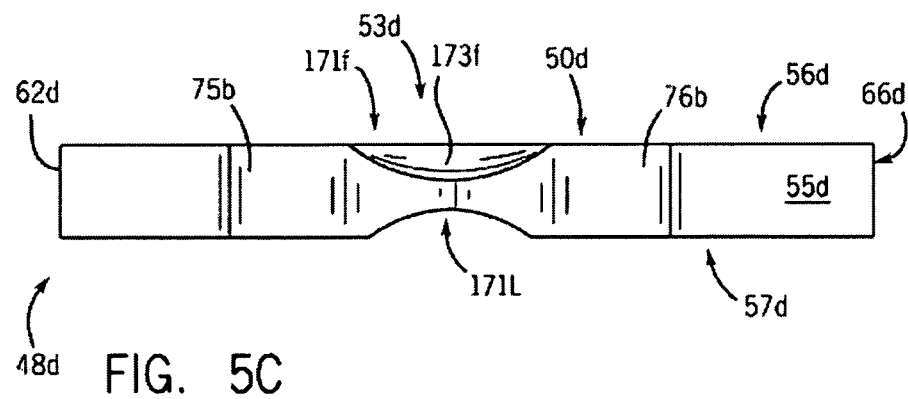
FIG. 5C is a front view of the barrier/barricade of FIG. 5B.

Turning now to FIGS. 5B and 5C, there is shown yet another embodiment of a barrier/barricade 48d which includes an elongated translucent (preferably transparent) elastic body 50d having a first end portion 51d, a second opposite end portion 52d, a middle portion 53d connecting the first end portion 51d and the second end portion 52d, a first side surface 54d, a second side surface 55d, a top surface 56d and a bottom surface 57d. The first end portion 51d extends to a first end surface 62d of the body 50d. The second end portion 52d extends to a second end surface 66d of the body 50d. The top surface 56d may include indicia 65d that indicate which side is placed upward away from the gingival during use.

In the barrier/barricade 48d, the first side surface 54d of the body 50d includes a curved protrusion 75f and a curved protrusion 76f. Likewise, the second side surface 55d of the body 50d includes a curved protrusion 75b and a curved protrusion 76b.

In barrier/barricade 48d, the first side surface 54d of the body 50d includes a first curved protrusion 77f located near an intermediate vertical plane of the body 50d. Likewise, the second side surface 55d of the body 50d includes a second curved protrusion 77b located near the intermediate vertical plane of the body 50d. The curved protrusions 77f, 77b are beneficial as they provide contact with tooth surface that may have inward decay due to the age of the patient. The barrier/barricade 48d can be formed from a translucent (preferably transparent) elastomeric material such as a silicone or polyurethane elastomer.

The surface of the barrier/barricade 48d can comprise an elastomeric material that allows the barrier/barricade 48d to be moved up or down a root or implant, toward or away from a tooth-to-restoration margin or implant-to-restoration margin during a restoration procedure. The surface of the barrier/barricade 48d can have a textured surface that allows the barrier/barricade 48d to be moved up or down a root or implant, toward or away from a tooth-to-restoration margin or implant-to-restoration margin during a restoration procedure. This allows the dentist to move the barrier/barricade 48d to adjust the distance of the top surface 56d of the body 50d of the barrier/barricade 48d from the tooth-to-restoration margin or implant-to-restoration margin.

The top surface 56d of the body 50d of the barrier/barricade 48d includes a first pair of upper side-by-side depressions 171f, 171b in the middle portion 53d of the body 50d. The first pair of upper side-by-side depressions 171f, 171b include inwardly curved inner surfaces 173f, 173b. The bottom surface 57d of the body 50d of the barrier/barricade 48d includes a lower concavity 171L in the middle portion 53d of the body 50d. The lower concavity 171L limits the application of undesired pressure on the interdental gingival when the barrier/barricade 48d is positioned between a patient's teeth.

Figure 5D:
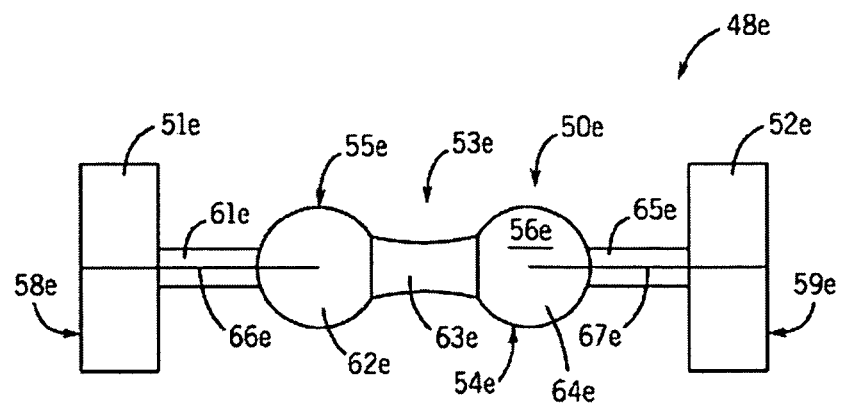
FIG. 5D is a top view of yet another embodiment of a barrier/barricade according to the invention.
Figure 5E:
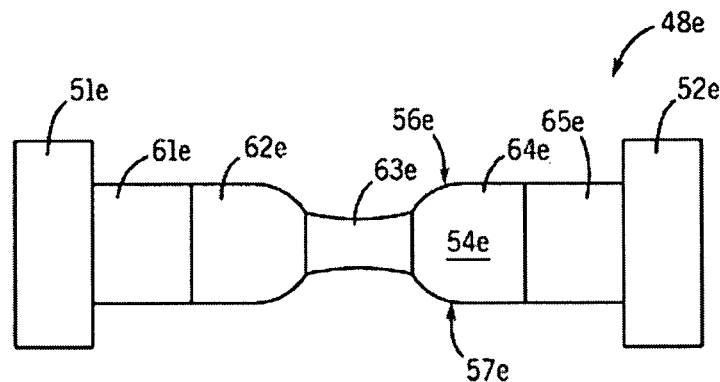
FIG. 5E is a front view of the barrier/barricade of FIG. 5D.
Figure 5F:
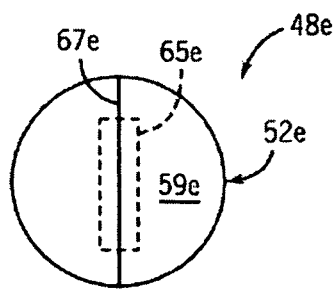
FIG. 5F is a side view of the barrier/barricade of FIG. 5D.

Turning now to FIGS. 5D to 5F, there is shown another embodiment of a barrier/barricade 48e which includes an elongated translucent (preferably transparent) elastic body 50e having a disc shaped first end portion 51e, a disc shaped second opposite end portion 52e, a middle portion 53e connecting the first end portion 51e and the second end portion 52e, a first side surface 54e, a second side surface 55e, a top surface 56e and a bottom surface 57e. The first end portion 51e extends to a first end surface 58e of the body 50e. The second end portion 52e extends to a second end surface 59e of the body 50e. The barrier/barricade 48e can be formed from a translucent (preferably transparent) elastomeric material such as a silicone or polyurethane elastomer.

The surface of the barrier/barricade 48e can comprise an elastomeric material that allows the barrier/barricade 48e to be moved up or down a root or implant, toward or away from a tooth-to-restoration margin or implant-to-restoration margin during a restoration procedure. The surface of the barrier/barricade 48e can have a textured surface that allows the barrier/barricade 48e to be moved up or down a root or implant, toward or away from a tooth-to-restoration margin or implant-to-restoration margin during a restoration procedure. This allows the dentist to move the barrier/barricade 48e to adjust the distance of the top surface 56e of the body 50e of the barrier/barricade 48 from the tooth-to-restoration margin or implant-to-restoration margin.

In the barrier/barricade 48e, the middle portion 53e includes a generally rectangular (in vertical cross-section) first section 61e, a first intermediate section 62e, a central rod-like section 63e, a second intermediate section 64e, and a generally rectangular (in vertical cross-section) second section 65e. As shown in the top view of FIG. 5D, the section of the first side surface 54e that is part of the first section 61e extends linearly inward from the first end portion 51e to the first intermediate section 62e. The section of the first side surface 54e that is part of the first intermediate section 62e extends in an outward arcuate manner from the first section 61e and then back inward in an arcuate manner to the central section 63e which is tapered inward near its center. The section of the first side surface 54e that is part of the second section 65e extends inward linearly from the second end portion 52e to the second intermediate section 64e. The section of the first side surface 54e that is part of the second intermediate section 64e extends in an outward arcuate manner from the second section 65e and then back inward in an arcuate manner to the central section 63e.

Likewise, the section of the second side surface 55e that is part of the first section 61e extends linearly inward from the first end portion 51e to the first intermediate section 62e. The section of the second side surface 55e that is part of the first intermediate section 62e extends in an outward arcuate manner from the first section 61e and then back inward in an arcuate manner to the central section 63e which is tapered inward near its center. The section of the second side surface 55e that is part of the second section 65e extends inward linearly from the second end portion 52e to the second intermediate section 64e. The section of the second side surface 55e that is part of the second intermediate section 64e extends in an outward arcuate manner from the second section 65e and then back inward in an arcuate manner to the central section 63e.

As shown in the side view of FIG. 5E, the section of the top surface 56e that is part of the first section 61e extends linearly inward from the first end portion 51e to the first intermediate section 62e and through part of the first intermediate section 62e. The section of the top surface 56e that is part of the inward section of the first intermediate section 62e extends inward in an arcuate manner to the central section 63e which is tapered inward near its center. The section of the top surface 56e that is part of the second section 65e extends linearly inward from the second end portion 52e to the second intermediate section 64e and through part of the second intermediate section 64e. The section of the top surface 56e that is part of the inward section of the second intermediate section 64e extends inward in an arcuate manner to the central section 63e.

Likewise, the section of the bottom surface 57e that is part of the first section 61e extends linearly inward from the first end portion 51e to the first intermediate section 62e and through part of the first intermediate section 62e. The section of the bottom surface 57e that is part of the inward section of the first intermediate section 62e extends inward in an arcuate manner to the central section 63e which is tapered inward near its center. The section of the bottom surface 57e that is part of the second section 65e extends linearly inward from the second end portion 52e to the second intermediate section 64e and through part of the second intermediate section 64e. The section of the bottom surface 57e that is part of the inward section of the second intermediate section 64e extends inward in an arcuate manner to the central section 63e.

The body 50e includes an area 66e of material weakness that extends toward the top surface 56e and extends toward the bottom surface 57e and extends to the first end surface 58e of the body 50e. The area 66e of material weakness extends from an inner portion of the first intermediate section 62e to the first end surface 58e of the body 50e. This allows the first end portion 51e, the first section 61e and part of the first intermediate section 62e to be separated into separate end members by application of a separation force at the area 66e of material weakness of the barrier/barricade 48e. Likewise, the body 50e includes an area 67e of material weakness that extends toward the top surface 56e and extends toward the bottom surface 57e and extends to the second end surface 59e of the body 50e. The area 67e of material weakness extends from an inner portion of the second intermediate section 64e to the second end surface 59e of the body 50e. This allows the second end portion 52e, the second section 65e and part of the second intermediate section 64e to be separated into separate end members by application of a separation force at the area 67e of material weakness of the barrier/barricade 48e.

Figure 5G:
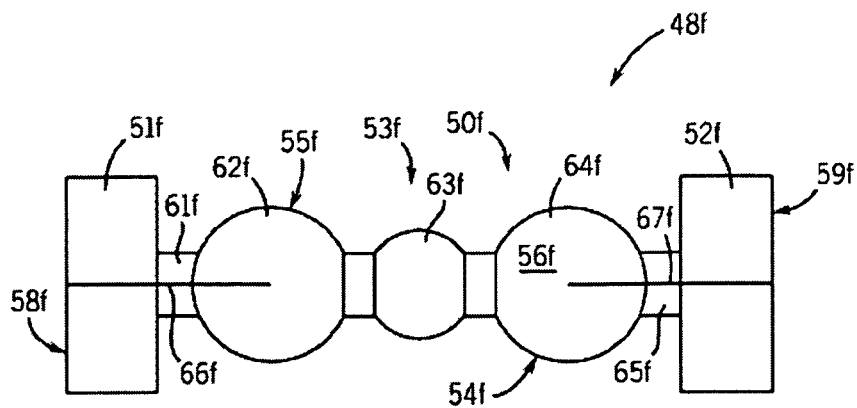
FIG. 5G is a top view of still another embodiment of a barrier/barricade according to the invention.
Figure 5H:
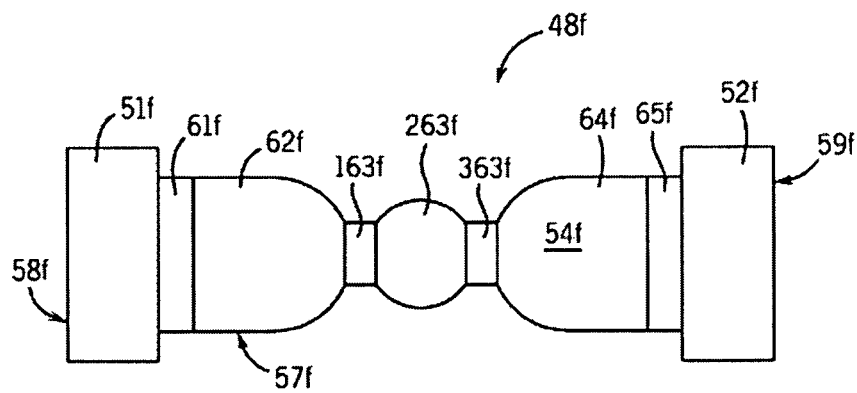
FIG. 5H is a front view of the barrier/barricade of FIG. 5G.
Figure 5I:
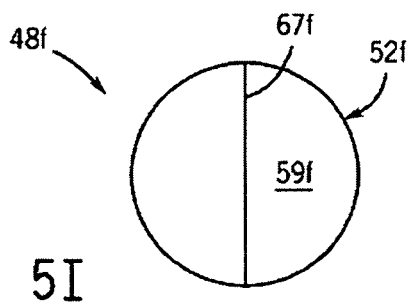
FIG. 5I is a side view of the barrier/barricade of FIG. 5G.

Turning now to FIGS. 5G to 5I, there is shown another embodiment of a barrier/barricade 48f which includes an elongated translucent (preferably transparent) elastic body 50f having a disc shaped first end portion 51f, a disc shaped second opposite end portion 52f, a middle portion 53f connecting the first end portion 51f and the second end portion 52f, a first side surface 54f, a second side surface 55f, a top surface 56f and a bottom surface 57f. The first end portion 51f extends to a first end surface 58f of the body 50f. The second end portion 52f extends to a second end surface 59f of the body 50f. The barrier/barricade 48f can be formed from a translucent (preferably transparent) elastomeric material such as a silicone or polyurethane elastomer.

The surface of the barrier/barricade 48f can comprise an elastomeric material that allows the barrier/barricade 48f to be moved up or down a root or implant, toward or away from a tooth-to-restoration margin or implant-to-restoration margin during a restoration procedure. The surface of the barrier/barricade 48f can have a textured surface that allows the barrier/barricade 48f to be moved up or down a root or implant, toward or away from a tooth-to-restoration margin or implant-to-restoration margin during a restoration procedure. This allows the dentist to move the barrier/barricade 48f to adjust the distance of the top surface 56f of the body 50f of the barrier/barricade 48f from the tooth-to-restoration margin or implant-to-restoration margin.

In the barrier/barricade 48f, the middle portion 53f includes a generally rectangular (in vertical cross-section) first section 61f, a first intermediate section 62f, a central section 63f, a second intermediate section 64f, and a generally rectangular (in vertical cross-section) second section 65f. As shown in the top view of FIG. 5G, the section of the first side surface 54f that is part of the first section 61f extends linearly inward from the first end portion 51f to the first intermediate section 62f. The section of the first side surface 54f that is part of the first intermediate section 62f extends in an outward arcuate manner from the first section 61f and then back inward in an arcuate manner to the central section 63f which has cylindrical end sections 163f, 363f on both sides of a generally spherical center section 263f. The section of the first side surface 54f that is part of the second section 65f extends inward linearly from the second end portion 52f to the second intermediate section 64f. The section of the first side surface 54f that is part of the second intermediate section 64f extends in an outward arcuate manner from the second section 65f and then back inward in an arcuate manner to the central tubular section 63f.

Likewise, the section of the second side surface 55f that is part of the first section 61f extends linearly inward from the first end portion 51f to the first intermediate section 62f. The section of the second side surface 55f that is part of the first intermediate section 62f extends in an outward arcuate manner from the first section 61f and then back inward in an arcuate manner to the central section 63f which has cylindrical end sections 163f, 363f on both sides of a generally spherical center section 263f. The section of the second side surface 55f that is part of the second section 65f extends inward linearly from the second end portion 52f to the second intermediate section 64f. The section of the second side surface 55f that is part of the second intermediate section 64f extends in an outward arcuate manner from the second section 65f and then back inward in an arcuate manner to the central tubular section 63f.

As shown in the side view of FIG. 5H, the section of the top surface 56f that is part of the first section 61f extends linearly inward from the first end portion 51f to the first intermediate section 62*f* and through part of the first intermediate section 62*f*. The section of the top surface 56*f* that is part of the inward section of the first intermediate section 62*f* extends inward in an arcuate manner to the central tubular section 63*f*. The section of the top surface 56*f* that is part of the second section 65*f* extends linearly inward from the second end portion 52*f* to the second intermediate section 64*f* and through part of the second intermediate section 64*f*. The section of the top surface 56*f* that is part of the inward section of the second intermediate section 64*f* extends inward in an arcuate manner to the central tubular section 63*f*.

Likewise, the section of the bottom surface 57*f* that is part of the first section 61*f* extends linearly inward from the first end portion 51*f* to the first intermediate section 62*f* and through part of the first intermediate section 62*f*. The section of the bottom surface 57*f* that is part of the inward section of the first intermediate section 62*f* extends inward in an arcuate manner to the central tubular section 63*f*. The section of the bottom surface 57*f* that is part of the second section 65*f* extends linearly inward from the second end portion 52*f* to the second intermediate section 64*f* and through part of the second intermediate section 64*f*. The section of the bottom surface 57*f* that is part of the inward section of the second intermediate section 64*f* extends inward in an arcuate manner to the central tubular section 63*f*.

The body 50*f* includes an area 66*f* of material weakness that extends toward the top surface 56*f* and extends toward the bottom surface 57*f* and extends to the first end surface 58*f* of the body 50*f*. The area 66*f* of material weakness extends from an inner portion of the first intermediate section 62*f* to the first end surface 58*f* of the body 50*f*. This allows the first end portion 51*f*, the first section 61*e* and part of the first intermediate section 62*f* to be separated into separate end members by application of a separation force at the area 66*f* of material weakness of the barrier/barricade 48*f*. Likewise, the body 50*f* includes an area 67*f* of material weakness that extends toward the top surface 56*f* and extends toward the bottom surface 57*f* and extends to the second end surface 59*f* of the body 50*f*. The area 67*f* of material weakness extends from an inner portion of the second intermediate section 64*f* to the second end surface 59*f* of the body 50*f*. This allows the second end portion 52*f*, the second section 65*f* and part of the second intermediate section 64*f* to be separated into separate end members by application of a separation force at the area 67*f* of material weakness of the barrier/barricade 48*f*.

Figure 5J:
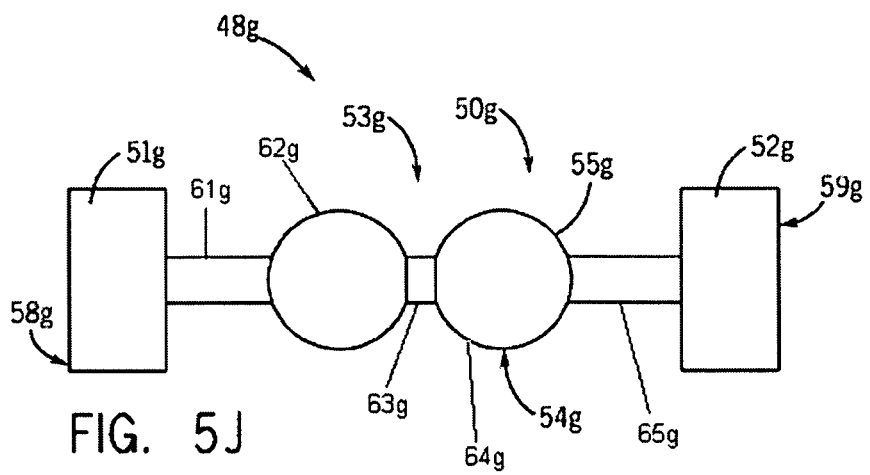
FIG. 5J is a top view of yet another embodiment of a barrier/barricade according to the invention.
Figure 5K:
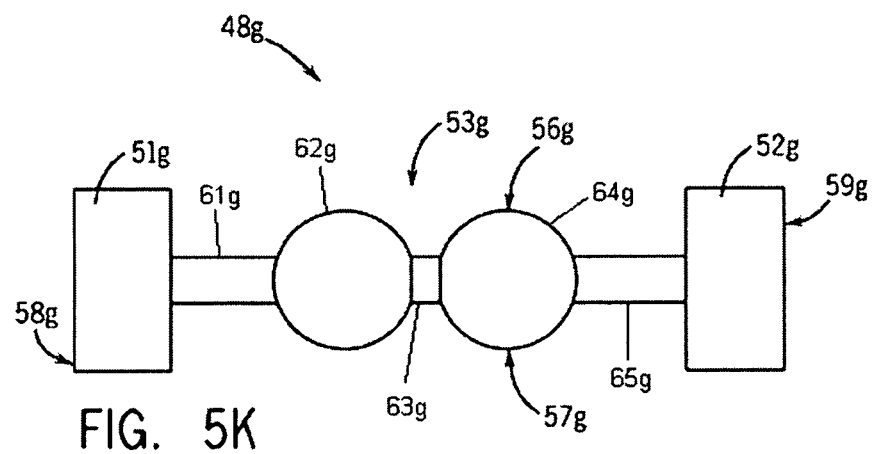
FIG. 5K is a front view of the barrier/barricade of FIG. 5J.
Figure 5L:
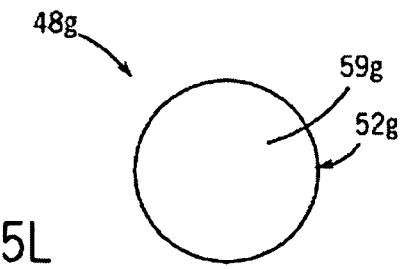
FIG. 5L is a side view of the barrier/barricade of FIG. 5J.
Figure 5M:
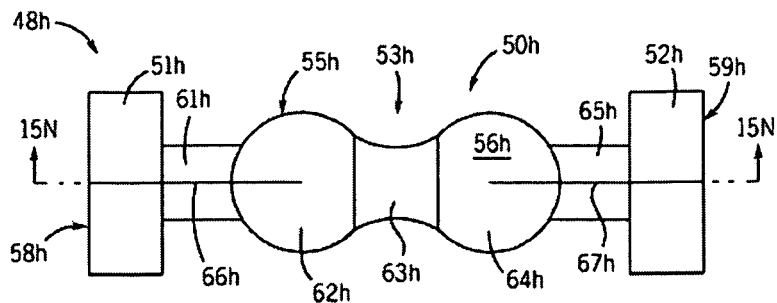
FIG. 5M is a top view of still another embodiment of a barrier/barricade according to the invention.

Turning now to FIGS. 5J to 5L, there is shown another embodiment of a barrier/barricade 48*g* which includes an elongated translucent (preferably transparent) elastic body 50*g* having a disc shaped first end portion 51*g*, a disc shaped second opposite end portion 52*g*, a middle portion 53*g* connecting the first end portion 51*g* and the second end portion 52*g*, a first side surface 54*g*, a second side surface 55*g*, a top surface 56*g* and a bottom surface 57*g*. The first end portion 51*g* extends to a first end surface 58*g* of the body 50*g*. The second end portion 52*g* extends to a second end surface 59*g* of the body 50*g*. The barrier/barricade 48*g* can be formed from a translucent (preferably transparent) elastomeric material such as a silicone or polyurethane elastomer.

The surface of the barrier/barricade 48*g* can comprise an elastomeric material that allows the barrier/barricade 48*g* to be moved up or down a root or implant, toward or away from a tooth-to-restoration margin or implant-to-restoration margin during a restoration procedure. The surface of the barrier/barricade 48*g* can have a textured surface that allows the barrier/barricade 48*g* to be moved up or down a root or implant, toward or away from a tooth-to-restoration margin or implant-to-restoration margin during a restoration procedure. This allows the dentist to move the barrier/barricade 48*g* to adjust the distance of the top surface 56*g* of the body 50*g* of the barrier/barricade 48*g* from the tooth-to-restoration margin or implant-to-restoration margin.

In the barrier/barricade 48*g*, the middle portion 53*g* includes a generally cylindrical first section 61*g*, a first spherical intermediate section 62*g*, a central cylindrical section 63*g*, a second spherical intermediate section 64*g*, and a generally cylindrical second section 65*g*.

Turning now to FIGS. 5M to 5P there is shown another embodiment of a barrier/barricade 48*h* which includes an elongated translucent (preferably transparent) elastic body 50*h* having a generally disc shaped first end portion 51*h*, a generally disc shaped second opposite end portion 52*h*, a middle portion 53*h* connecting the first end portion 51*h* and the second end portion 52*h*, a first side surface 54*h*, a second side surface 55*h*, a top surface 56*h* and a bottom surface 57*h*. The first end portion 51*h* extends to a first end surface 58*h* of the body 50*h*. The second end portion 52*h* extends to a second end surface 59*h* of the body 50*h*. The barrier/barricade 48*h* can be formed from a translucent (preferably transparent) elastomeric material such as a silicone or polyurethane elastomer.

The surface of the barrier/barricade 48*h* can comprise an elastomeric material that allows the barrier/barricade 48*h* to be moved up or down a root or implant, toward or away from a tooth-to-restoration margin or implant-to-restoration margin during a restoration procedure. The surface of the barrier/barricade 48*h* can have a textured surface that allows the barrier/barricade 48*h* to be moved up or down a root or implant, toward or away from a tooth-to-restoration margin or implant-to-restoration margin during a restoration procedure. This allows the dentist to move the barrier/barricade 48*h* to adjust the distance of the top surface 56*h* of the body 50*h* of the barrier/barricade 48*h* from the tooth-to-restoration margin or implant-to-restoration margin.

In the barrier/barricade 48*h*, the middle portion 53*h* includes a generally rectangular (in vertical cross-section) first section 61*h*, a first intermediate section 62*h*, a central rod-like section 63*h*, a second intermediate section 64*h*, and a generally rectangular (in vertical cross-section) second section 65*h*. As shown in the top view of FIG. 5M, the section of the first side surface 54*h* that is part of the first section 61*h* extends linearly inward from the first end portion 51*h* to the first intermediate section 62*h*. The section of the first side surface 54*h* that is part of the first intermediate section 62*h* extends in an outward arcuate manner from the first section 61*h* and then back inward in an arcuate manner to the central section 63*h* which is tapered inward near its center. The section of the first side surface 54*h* that is part of the second section 65*h* extends inward linearly from the second end portion 52*h* to the second intermediate section 64*h*. The section of the first side surface 54*h* that is part of the second intermediate section 64*h* extends in an outward arcuate manner from the second section 65*h* and then back inward in an arcuate manner to the central section 63*h*.

Likewise, the section of the second side surface 55*h* that is part of the first section 61*h* extends linearly inward from the first end portion 51*h* to the first intermediate section 62*h*. The section of the second side surface 55*h* that is part of the first intermediate section 62*h* extends in an outward arcuate manner from the first section 61*h* and then back inward in an arcuate manner to the central section 63*h* which is tapered inward near its center. The section of the second side surface 55*h* that is part of the second section 65*h* extends inward linearly from the second end portion 52*h* to the second intermediate section 64*h*. The section of the second side surface 55h that is part of the second intermediate section 64h extends in an outward arcuate manner from the second section 65h and then back inward in an arcuate manner to the central section 63h.

Figure 5N:
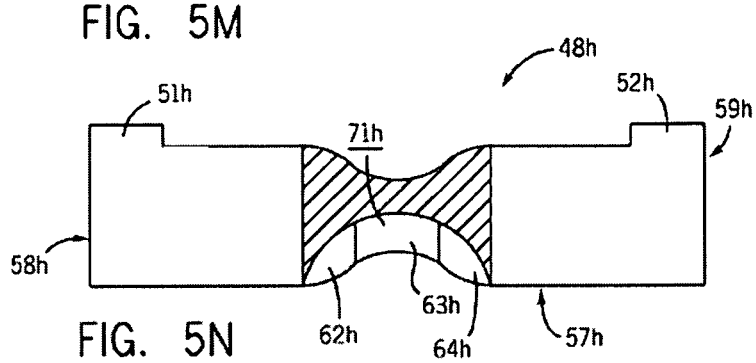
FIG. 5N is a cross-sectional view of the barrier/barricade of FIG. 5M taken along line 5N-5N of FIG. 5M.
Figure 5O:
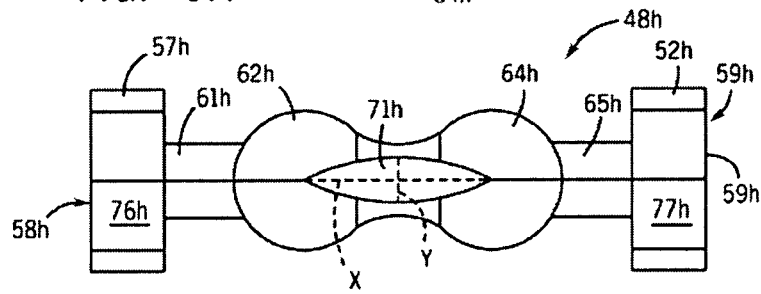
FIG. 5O is a bottom view of the barrier/barricade of FIG. 5M.
Figure 5P:
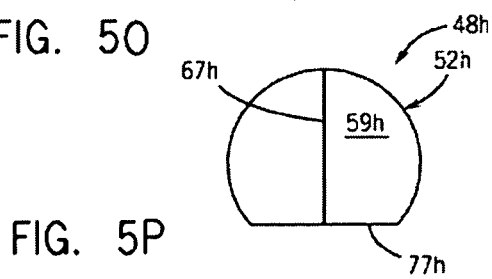
FIG. 5P is a side view of the barrier/barricade of FIG. 5M.
Figure 5Q:
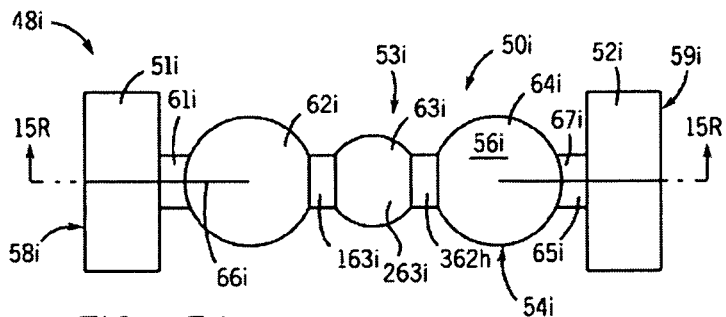
FIG. 5Q is a top view of yet another embodiment of a barrier/barricade according to the invention.

As shown in the side view of FIG. 5N, the section of the top surface 56h that is part of the first section 61h extends linearly inward from the first end portion 51h to the first intermediate section 62h and through part of the first intermediate section 62h. The section of the top surface 56h that is part of the inward section of the first intermediate section 62h extends inward in an arcuate manner to the central section 63e which is tapered inward near its center. The section of the top surface 56h that is part of the second section 65h extends linearly inward from the second end portion 52h to the second intermediate section 64h and through part of the second intermediate section 64h. The section of the top surface 56h that is part of the inward section of the second intermediate section 64h extends inward in an arcuate manner to the central section 63h.

Likewise, the section of the bottom surface 57h that is part of the first section 61h extends linearly inward from the first end portion 51h to the first intermediate section 62h and through part of the first intermediate section 62h. The section of the bottom surface 57h that is part of the inward section of the first intermediate section 62h extends inward in an arcuate manner to the central section 63h which is tapered inward near its center. The section of the bottom surface 57h that is part of the second section 65h extends linearly inward from the second end portion 52h to the second intermediate section 64h and through part of the second intermediate section 64h. The section of the bottom surface 57h that is part of the inward section of the second intermediate section 64e extends inward in an arcuate manner to the central section 63h.

The body 50h includes an area 66h of material weakness that extends toward the top surface 56h and extends toward the bottom surface 57h and extends to the first end surface 58h of the body 50h. The area 66h of material weakness extends from an inner portion of the first intermediate section 62h to the first end surface 58h of the body 50h. This allows the first end portion 51h, the first section 61h and part of the first intermediate section 62h to be separated into separate end members by application of a separation force at the area 66h of material weakness of the barrier/barricade 48h. Likewise, the body 50h includes an area 67h of material weakness that extends toward the top surface 56h and extends toward the bottom surface 57h and extends to the second end surface 59h of the body 50h. The area 67h of material weakness extends from an inner portion of the second intermediate section 64h to the second end surface 59h of the body 50h. This allows the second end portion 52h, the second section 65h and part of the second intermediate section 64h to be separated into separate end members by application of a separation force at the area 67h of material weakness of the barrier/barricade 48h.

In the barrier/barricade 48h, there is an inward concavity 71h in the bottom surface 57h in an inward section of the first intermediate section 62h, the central section 63h, and an inward section of the second intermediate section 64h. The inward concavity 71h has a longitudinal axis X and a lateral axis Y transverse to the longitudinal axis X. The longitudinal axis X extend toward the first end portion 51h and the second end portion 52h. The longitudinal axis X is longer than the lateral axis Y. The 71h limits the application of undesired pressure on the interdental gingival when the barrier/barricade 48h is positioned between a patient's teeth. Also, the first end portion 51h has a flat bottom surface 76h, and the second end portion 52h has a flat bottom surface 77h.

Turning now to FIGS. 5Q to 5T, there is shown another embodiment of a barrier/barricade 48i which includes an elongated translucent (preferably transparent) elastic body 50i having a generally disc shaped first end portion 51i, a generally disc shaped second opposite end portion 52i, a middle portion 53i connecting the first end portion 51i and the second end portion 52i, a first side surface 54i, a second side surface 55i, a top surface 56i and a bottom surface 57i. The first end portion 51i extends to a first end surface 58i of the body 50i. The second end portion 52i extends to a second end surface 59i of the body 50i. The barrier/barricade 48i can be formed from a translucent (preferably transparent) elastomeric material such as a silicone or polyurethane elastomer.

The surface of the barrier/barricade 48i can comprise an elastomeric material that allows the barrier/barricade 48i to be moved up or down a root or implant, toward or away from a tooth-to-restoration margin or implant-to-restoration margin during a restoration procedure. The surface of the barrier/barricade 48i can have a textured surface that allows the barrier/barricade 48i to be moved up or down a root or implant, toward or away from a tooth-to-restoration margin or implant-to-restoration margin during a restoration procedure. This allows the dentist to move the barrier/barricade 48 to adjust the distance of the top surface 56i of the body 50i of the barrier/barricade 48 from the tooth-to-restoration margin or implant-to-restoration margin.

In the barrier/barricade 48i, the middle portion 53i includes a generally rectangular (in vertical cross-section) first section 61i, a first intermediate section 62i, a central section 63i, a second intermediate section 64i, and a generally rectangular (in vertical cross-section) second section 65i. As shown in the top view of FIG. 5Q, the section of the first side surface 54i that is part of the first section 61i extends linearly inward from the first end portion 51i to the first intermediate section 62i. The section of the first side surface 54i that is part of the first intermediate section 62i extends in an outward arcuate manner from the first section 61i and then back inward in an arcuate manner to the central section 63i which has cylindrical end sections 163i, 363i on both sides of a generally spherical center section 263i. The section of the first side surface 54i that is part of the second section 65i extends inward linearly from the second end portion 52i to the second intermediate section 64i. The section of the first side surface 54i that is part of the second intermediate section 64i extends in an outward arcuate manner from the second section 65i and then back inward in an arcuate manner to the central tubular section 63i.

Likewise, the section of the second side surface 55i that is part of the first section 61i extends linearly inward from the first end portion 51i to the first intermediate section 62i. The section of the second side surface 55i that is part of the first intermediate section 62i extends in an outward arcuate manner from the first section 61i and then back inward in an arcuate manner to the central section 63i which has cylindrical end sections 163i, 363i on both sides of a generally spherical center section 263i. The section of the second side surface 55i that is part of the second section 65i extends inward linearly from the second end portion 52i to the second intermediate section 64i. The section of the second side surface 55i that is part of the second intermediate section 64i extends in an outward arcuate manner from the second section 65i and then back inward in an arcuate manner to the central tubular section 63i.

Figure 5R:
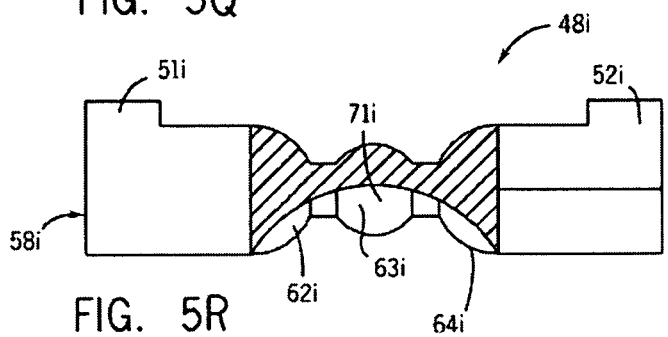
FIG. 5R is a cross-sectional view of the barrier/barricade of FIG. 5Q taken along line 5R-5R of FIG. 5Q.
Figure 5S:
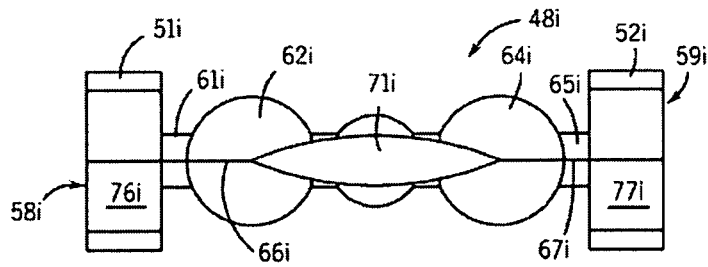
FIG. 5S is a bottom view of the barrier/barricade of FIG. 5Q.
Figure 5T:
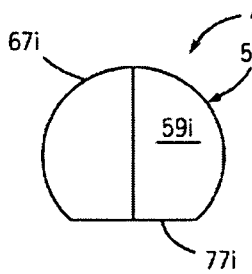
FIG. 5T is a side view of the barrier/barricade of FIG. 5Q.
Figure 5U:
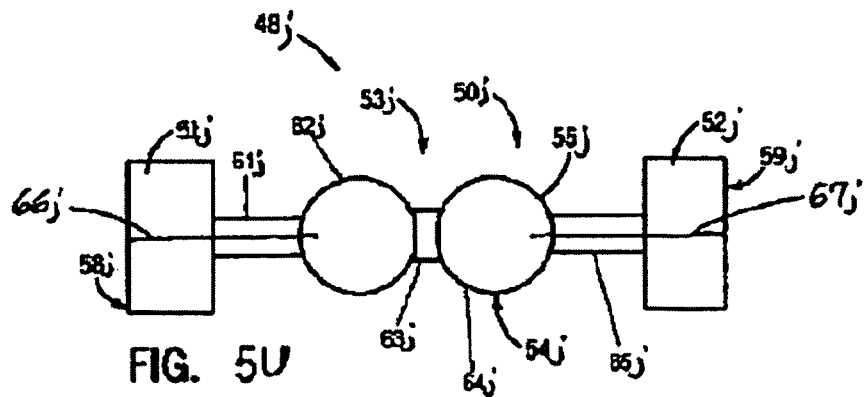
FIG. 5U is a top view of still another embodiment of a barrier/barricade according to the invention.
Figure 5V:
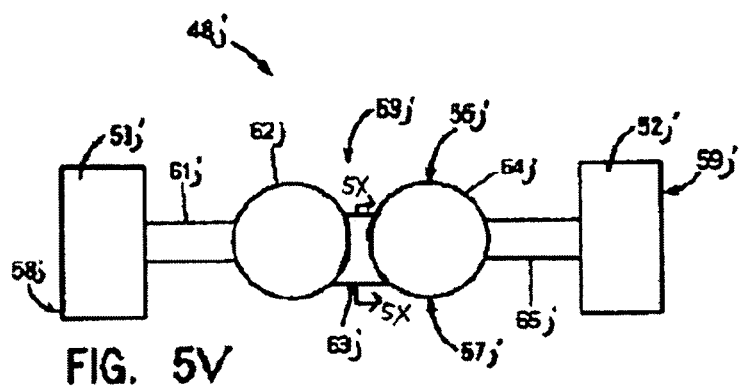
FIG. 5V is a front view of the barrier/barricade of FIG. 5U.
Figure 5W:
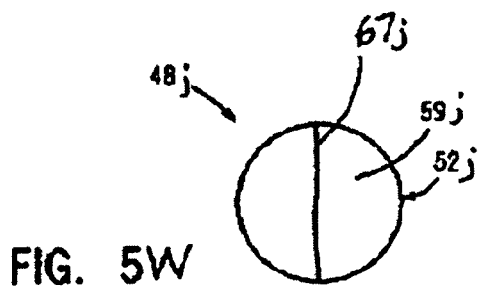
FIG. 5W is a side view of the barrier/barricade of FIG. 5U.

As shown in the side view of FIG. 5R, the section of the top surface 56i that is part of the first section 61i extends linearly inward from the first end portion 51i to the first intermediate section 62i and through part of the first intermediate section 62i. The section of the top surface 56i that is part of the inward section of the first intermediate section 62i extends inward in an arcuate manner to the central tubular section 63i. The section of the top surface 56i that is part of the second section 65i extends linearly inward from the second end portion 52i to the second intermediate section 64i and through part of the second intermediate section 64i. The section of the top surface 56i that is part of the inward section of the second intermediate section 64i extends inward in an arcuate manner to the central tubular section 63i.

Likewise, the section of the bottom surface 57i that is part of the first section 61i extends linearly inward from the first end portion 51i to the first intermediate section 62i and through part of the first intermediate section 62i. The section of the bottom surface 57i that is part of the inward section of the first intermediate section 62i extends inward in an arcuate manner to the central tubular section 63i. The section of the bottom surface 57i that is part of the second section 65i extends linearly inward from the second end portion 52i to the second intermediate section 64i and through part of the second intermediate section 64i. The section of the bottom surface 57i that is part of the inward section of the second intermediate section 64i extends inward in an arcuate manner to the central tubular section 63i.

The body 50i includes an area 66i of material weakness that extends toward the top surface 56i and extends toward the bottom surface 57i and extends to the first end surface 58i of the body 50i. The area 66i of material weakness extends from an inner portion of the first intermediate section 62i to the first end surface 58i of the body 50i. This allows the first end portion 51i, the first section 61i and part of the first intermediate section 62i to be separated into separate end members by application of a separation force at the area 66i of material weakness of the barrier/barricade 48i. Likewise, the body 50i includes an area 67i of material weakness that extends toward the top surface 56i and extends toward the bottom surface 57i and extends to the second end surface 59i of the body 50i. The area 67i of material weakness extends from an inner portion of the second intermediate section 64i to the second end surface 59i of the body 50i. This allows the second end portion 52i the second section 65i and part of the second intermediate section 64i to be separated into separate end members by application of a separation force at the area 67i of material weakness of the barrier/barricade 48i.

In the barrier/barricade 48i, there is an inward concavity 71i in the bottom surface 57i in an inward section of the first intermediate section 62i, the central section 63i, and an inward section of the second intermediate section 64i. The 71i limits the application of undesired pressure on the interdental gingival when the barrier/barricade 48h is positioned between a patient's teeth. Also, the first end portion 51i has a flat bottom surface 76i, and the second end portion 52i has a flat bottom surface 77i.

Turning now to FIGS. 5U to 5X, there is shown another embodiment of a barrier/barricade 48j which includes an elongated translucent (preferably transparent) elastic body 50j having a disc shaped first end portion 51j, a disc shaped second opposite end portion 52j, a middle portion 53j connecting the first end portion 51j and the second end portion 52j, a first side surface 54j, a second side surface 55j, a top surface 56j, and a bottom surface 57j. The first end portion 51j extends to a first end surface 58j of the body 50j. The second end portion 52j extends to a second end surface 59j of the body 50j. The barrier/barricade 48j can be formed from a translucent (preferably transparent) elastomeric material such as a silicone or polyurethane elastomer.

The surface of the barrier/barricade 48j can comprise an elastomeric material that allows the barrier/barricade 48j to be moved up or down a root or implant, toward or away from a tooth-to-restoration margin or implant-to-restoration margin during a restoration procedure. The surface of the barrier/barricade 48j can have a textured surface that allows the barrier/barricade 48j to be moved up or down a root or implant, toward or away from a tooth-to-restoration margin or implant-to-restoration restoration margin during a restoration procedure. This allows the dentist to move the barrier/barricade 48j to adjust the distance of the top surface 56j of the body 50j of the barrier/barricade 48j from the tooth-to-restoration margin or implant-to-restoration margin.

Figure 5X:
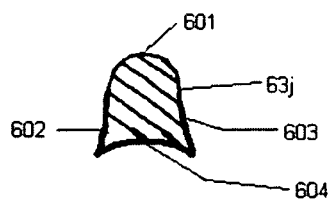
FIG. 5X is a cross-sectional view of the central portion of the barrier/barricade of FIGS. 5U-5X taken along line 5X-5X of FIG. 5V.

In the barrier/barricade 48j, the middle portion 53j includes a generally cylindrical first section 61j, a first spherical intermediate section 62j, a central section 63j (shown in vertical cross-section in FIG. 5X), a second spherical intermediate section 64j, and a generally cylindrical second section 65j. Referring to FIG. 5X, the central section 63j has an arcuate top surface 601 and side surfaces 602, 603 that are concave at the lower portion. The bottom corners of the side surfaces 602, 603 are joined by an upwardly concave bottom surface 604. The concave side surfaces 602, 603 of the central section 63j of the barrier/barricade 48j fit snugly against the interproximal surface 31 of the tooth 12 and the interproximal surface of the tooth 34 respectively. The upwardly concave bottom surface 604 of the central section 63j of the barrier/barricade 48j fits snugly on the gingiva and compresses and displaces gingiva when the barrier/barricade 48j is positioned between the teeth 12 and 34.

The body 50j includes an area 66j of material weakness that extends toward the top surface 56j and extends toward the bottom surface 57j and extends to the first end surface 58j of the body 50j. The area 66j of material weakness extends from an inner portion of the first intermediate section 62j to the first end surface 58j of the body 50j. This allows the first end portion 51j, the first section 61j and part of the first intermediate section 62j to be separated into separate end members by application of a separation force at the area 66j of material weakness of the barrier/barricade 48j. Likewise, the body 50j includes an area 67j of material weakness that extends toward the top surface 56j and extends toward the bottom surface 57j and extends to the second end surface 59j of the body 50j. The area 67j of material weakness extends from an inner portion of the second intermediate section 64j to the second end surface 59j of the body 50j. This allows the second end portion 52j, the second section 65j and part of the second intermediate section 64j to be separated into separate end members by application of a separation force at the area 67j of material weakness of the barrier/barricade 48j.

All of the barrier/barricades 48A, 48B, 48d, 48e, 48f, 48g, 48h, 48i, 48j may be positioned as shown in FIG. 1 wherein the dentist stretches the barrier/barricade in directions A and B shown in FIG. 1 by way of a pliers or simply pulling apart the end portions and of the barrier/barricade in directions A and B shown in FIG. 1. The stretching of the barrier/barricade leads to a thinning of the middle portion of the barrier/barricade such that the barrier/barricade can be inserted between teeth 12 and 34 by movement in direction C of FIG. 1. Prewedging of the teeth 12 and 34 may ease insertion of the barrier/barricade between the teeth 12 and 34. The barrier/barricade covers gingiva and a surface section 29 of the tooth 12 being restored to prevent cement from bonding to the section of the tooth. This eliminates the need to remove hardened cement from this section of the tooth.

After the barrier/barricade (any of 48, 48A, 48B, 48d, 48e, 48f, 48g, 48h, 48i, 48j) is placed between teeth 12 and 34, the dentist acid etches the mating surface 22 of the tooth 12 to facilitate fusion of the fixed restoration 24 to the tooth 12. An appropriate adhesive or cement 28 is applied to the underside mating surface 26 of the restoration 24 and/or the mating surface 22 of the tooth 12. The restoration 24 is pressed into place and the adhesive or cement 28 is allowed to cure, usually using a curing light. Looking at FIG. 2, the barrier/barricade 48 covers gingiva (the dashed lines in FIG. 2) and a surface section 29 of the interproximal surface 31 of the tooth 12. The barrier/barricade 48 covers the top portion of the surface section 29 up to about 0.75 millimeters or less from the tooth-to-restoration margin 32. Therefore, the adhesive or cement 28 cannot extend far (preferably 0.75 millimeters or less) beyond the tooth-to-restoration margin 32 after the adhesive or cement 28 is allowed to cure. In certain applications, the barrier/barricade 48 may cover the top portion of the surface section 29 up to about 5 millimeters or less from the tooth-to-restoration margin 32, or up to about 4 millimeters or less from the tooth-to-restoration margin 32, or up to about 3 millimeters or less from the tooth-to-restoration margin 32, or up to about 2 millimeters or less from the tooth-to-restoration margin 32. Furthermore, the surface of the barrier/barricade 48 can comprise an elastomeric material and/or have a textured surface that allows the barrier/barricade 48 to be moved up or down a root or implant, toward or away from a tooth-to-restoration margin or implant-to-restoration margin during a restoration procedure. This allows the dentist to move the barrier/barricade 48 to adjust the distance of the top surface 56 of the body 50 of the barrier/barricade 48 from the tooth-to-restoration margin 32 or implant-to-restoration margin. As a result, the dentist can position the top surface 56 of the body 50 of the barrier/barricade 48 such that the dentist does not have to remove much excess hardened cement from the interproximal surface 31 of the tooth 12 after the installation of the restoration 24. Also, the separation of the teeth 12 and 34 provided by the barrier/barricade 48 provides for easy cleanup of excess cement between the teeth 12 and 34.

In another embodiment of the invention, a fixed restoration having a first mating surface substantially conforming to a second mating surface of the tooth is provided. A flowable curable barrier/barricade material is applied to a surface section of the tooth being restored and adjacent gingiva. The barrier/barricade material is cured on the surface section of the tooth and adjacent gingiva. The cured barrier/barricade material covers a section of the tooth being restored to form a barricade to prevent cement from bonding to the section of the tooth. This eliminates the need to remove hardened cement from this section of the tooth. The cured barrier/barricade material also forms a gingiva barrier to prevent gingiva laceration, gingiva abrasion and/or fluid (e.g., blood, saliva) contamination. In the method, a cement is applied to the first mating surface of the fixed restoration and/or to the second mating surface of the tooth, and the first mating surface and the second mating surface are positioned adjacent each other to seat the fixed restoration on the tooth. In the method, the tooth-to-restoration margin is located adjacent the surface section having the cured barrier/barricade material. The cured barrier/barricade material may be removed after the restoration is complete.

The flowable curable barrier/barricade material may be delivered using a syringe or may be placed using another dental instrument. The barrier/barricade material can comprise (i) a monomer or prepolymer and (ii) a curing agent that polymerizes the monomer or crosslinks the prepolymer. The monomer or prepolymer and curing agent can be delivered together after storage in separate compartments. The barrier/barricade material can include a solvent, and the barrier/barricade material can cure during evaporation of the solvent. The barrier/barricade material may also be light curable with a dental curing light.

Examples of suitable monomers include acrylates, methacrylates, alkylmethacrylates, alklyhydroxymethacrylates, and alkylaminomethacrylates. These may be cured using, for example, photoinitiator curing agents such as camphorquinone; benzoin methyl ether; 2-hydroxy-2-methyl-1-phenyl-1-propanone; diphenyl 2,4,6-trimethylbenzoyl phosphine oxide; benzoin ethyl ether; benzophenone; 9,10-anthraquinone, and equivalents. A curing light can accelerate the curing time. Monomer levels in the barrier/barricade material can be, for example, 50-99 percent by weight of the total weight of the composition. Curing agent levels in the barrier/barricade material can be, for example, 0.0001-10 percent by weight of the total weight of the composition. Carrier solvents and fillers (e.g., oxide particles) can be used in the curable barrier/barricade material.

Example prepolymers include vinyl chloride and/or vinyl acetate prepolymers, and the prepolymers may be applied in an organic solvent solution. Example organic solvents include acetone, methyl ethyl ketone, diethyl ether, diisopropyl ether, ethanol, n-propanol, isopropanol, tetrahydrofuran, methyl acetate, ethyl acetate, n-propyl acetate, isopropyl acetate, n-butyl acetate, and isobutyl acetate. Prepolymer levels in the barrier/barricade material can be, for example, 1-99 percent by weight of the total weight of the composition. Solvent levels in the barrier/barricade material can be, for example, 1-99 percent by weight of the total weight of the composition.

Thus, the invention provides a system, kit, and devices for the management of interproximal areas for traditional cementation and/or bonding of dental crowns, onlays, inlays, veneers and bridges. A device according to the invention forms a barricade to prevent cement from bonding to regions where hardened cement is undesired. The device also forms a gingiva barrier to prevent gingiva laceration, gingiva abrasion and fluid (e.g., blood, saliva) contamination. The barrier lightly separates the teeth, permitting full seating and snug contacts. By providing a biomimetic barrier, the barrier prevents contamination and keeps cement from spreading onto neighboring teeth. The outcome is less operator stress, and better inlay/onlay seatings.

Although the invention has been described in considerable detail with reference to certain embodiments, one skilled in the art will appreciate that the present invention can be practiced by other than the described embodiments, which have been presented for purposes of illustration and not of limitation. Therefore, the scope of the appended claims should not be limited to the description of the embodiments contained herein.

What is claimed is:

1. A method for restoring a natural or artificial tooth, the method comprising:
   providing a fixed restoration having a first mating surface substantially conforming to a second mating surface of the tooth;
   positioning a barrier in contact with the tooth being restored to cover an interproximal surface section of the tooth being restored, the barrier comprising an elongated elastic body;
   applying a cement to the first mating surface of the fixed restoration and/or to the second mating surface of the tooth; and
   positioning the first mating surface and the second mating surface adjacent each other, wherein the body of the barrier has a first end portion, a second opposite end portion, a side surface, a top surface, and a middle portion connecting the first end portion and the second end portion, the middle portion including a first section attached to the first end portion, a first intermediate section attached to a central section and the first section such that the first intermediate section and the first end portion are in spaced relationship, a second intermediate section attached to the central section opposite the first end portion, and a second section attached to the second intermediate section and the second opposite end portion such that the second intermediate section and the second opposite end portion are in spaced relationship, wherein the side surface of the body includes a first protrusion on the first intermediate section, the first protrusion being spaced inward from a first end surface of the first end portion of the body, the first protrusion extending outward laterally in relation to the top surface from an inner end of the first section, the first protrusion extending outward from a first outer end of the central section, and wherein the side surface of the body further includes a second protrusion on the second intermediate section, the second protrusion being spaced inward from a second end surface of the second opposite end portion of the body, the second protrusion extending outward laterally in relation to the top surface from an inner end of the second section, the second protrusion extending outward from a second outer end of the central section, and wherein the first protrusion and the second protrusion contact the tooth being restored when the barrier is positioned in contact with the tooth being restored, and wherein the first end portion extends outward laterally in relation to the top surface from an outer end of the first section of the middle portion, wherein the second end portion extends outward laterally in relation to the top surface from an outer end of the second section of the middle portion, and wherein the first section is between the first end portion and the first protrusion, the first end portion is wider than the first section, and the first protrusion is wider than the first section, and wherein the second section is between the second end portion and the second protrusion, the second end portion is wider than the second section, and the second protrusion is wider than the second section.

2. The method of claim 1 wherein:
the fixed restoration is selected from crowns, onlays, inlays, veneers, and bridges.

3. The method of claim 1 wherein:
the fixed restoration comprises a material selected from porcelain, metallic materials, porcelain fused to a metallic material, composite materials, polymeric materials, and ceramic materials.

4. The method of claim 1 wherein:
the central section includes concave lower side surfaces.

5. The method of claim 4 wherein:
the central section includes a concave bottom surface.

6. The method of claim 1 wherein:
the body of the barrier is dimensioned such that a bottom surface of the body contacts gingiva and the top surface of the barrier is positioned within 5 millimeters of a margin selected from a tooth-to-restoration margin, an implant-to-restoration margin, and an implant abutment-to-restoration margin when the barrier is positioned in contact with the tooth.

7. The method of claim 1 wherein:
the body of the barrier is dimensioned to create separation of the tooth being restored and an adjacent tooth.

8. The method of claim 1 wherein:
the top surface of the barrier is positioned within 5 millimeters of a margin selected from a tooth-to-restoration margin, an implant-to-restoration margin, and an implant abutment-to-restoration margin when the barrier is positioned in contact with the tooth.

9. The method of claim 1 wherein:
the barrier has an elastomeric surface that allows the barrier to be moved toward or away from a margin selected from a tooth-to-restoration margin, an implant-to-restoration margin, and an implant abutment-to-restoration margin.

* * * * *